(12) United States Patent
Krämer

(10) Patent No.: US 6,260,419 B1
(45) Date of Patent: Jul. 17, 2001

(54) METHOD AND DEVICE FOR CONDUCTING A HARDNESS TEST ON TEST SPECIMENS, ESPECIALLY TABLETS OR PILLS

(76) Inventor: Norbert Krämer, Röntgenstrasse 68, D-64291 Darmstad (DE)

( * ) Notice: Subject to any disclaimer, the term of this patent is extended or adjusted under 35 U.S.C. 154(b) by 0 days.

(21) Appl. No.: 09/424,437
(22) PCT Filed: May 14, 1998
(86) PCT No.: PCT/DE98/01345
    § 371 Date: Nov. 23, 1999
    § 102(e) Date: Nov. 23, 1999
(87) PCT Pub. No.: WO98/53298
    PCT Pub. Date: Nov. 26, 1998

(30) Foreign Application Priority Data

May 23, 1997 (DE) ............................................. 197 21 656
Jun. 9, 1997 (DE) ............................................. 197 24 121
Oct. 7, 1997 (DE) ............................................. 197 44 227

(51) Int. Cl.$^7$ .................................................. G01N 3/08
(52) U.S. Cl. ................................................. 73/821; 73/78
(58) Field of Search .............................. 73/818, 819, 821, 73/824, 825, 78, 81

(56) References Cited

U.S. PATENT DOCUMENTS

| 3,630,073 | * | 12/1971 | Michel | 73/818 |
|---|---|---|---|---|
| 3,665,757 | * | 5/1972 | Hoag | 73/818 |
| 3,757,566 | * | 9/1973 | Flury | 73/821 |
| 4,236,413 | * | 12/1980 | Schmid et al. | 73/821 |
| 4,542,646 | * | 9/1985 | Smith et al. | 73/78 |
| 4,641,534 | | 2/1987 | Schneider et al. | |
| 4,884,463 | | 12/1989 | Kay. | |
| 5,555,768 | | 9/1996 | Shaffer et al. | |

FOREIGN PATENT DOCUMENTS 4241985   6/1994 (DE).

* cited by examiner

*Primary Examiner*—Max Noori
(74) *Attorney, Agent, or Firm*—Horst M. Kasper

(57) ABSTRACT

The invention relates to a method and a device for conducting a hardness test on test specimens (7, 7', 7", 28, 28'), specially tablets. The direction in which the hardness test is conducted by pressing a pressure piston (3, 3', 3", 26, 26') and a thrust bearing (4, 4', 4", 27, 27') against each other, is actively adjusted to the preferred axis (12, 2', 12") of the test specimen (7, 7', 7", 28, 28'). This enables measurement errors to be avoided, specially in relation to asymmetrical test specimens, resulting from variations in the direction of testing (13, 13'). The position and orientation of the test specimen (7, 7', 7", 28, 28') are detected by means of a position signaling device (10). Subsequently, the testing direction (13) is adjusted to the preferred axis (12, 12', 12") by actively rotating the pressure piston (3, 3', 3", 26, 26') and the thrust bearing (4, 4', 4", 27, 27') on a stationary test bench (1, 1', 1", 32, 32') and a stationary test specimen (7, 7', 7", 28, 28').

20 Claims, 5 Drawing Sheets

Figure 1:
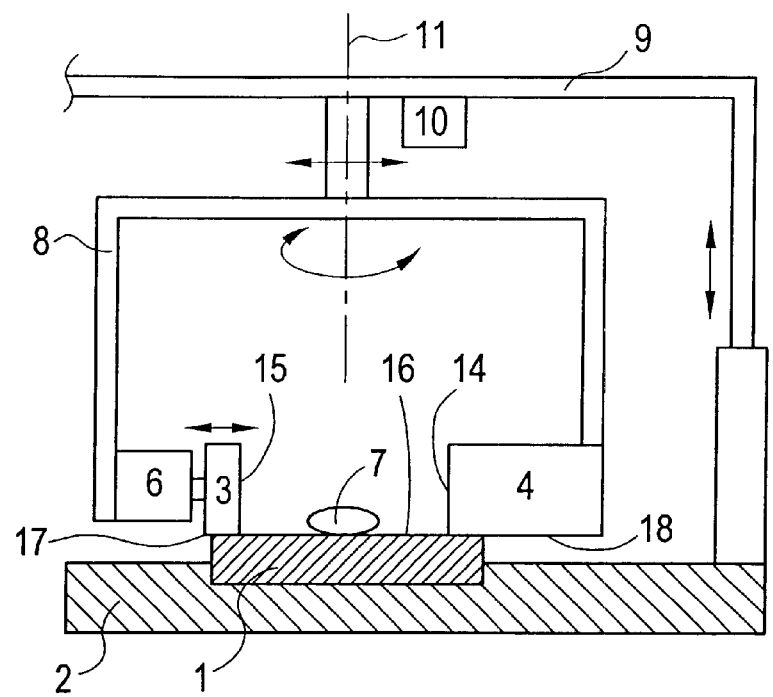

METHOD AND DEVICE FOR CONDUCTING A HARDNESS TEST ON TEST SPECIMENS, ESPECIALLY TABLETS OR PILLS

TECHNICAL AREA

The invention relates to a process and a device for conducting a hardness test on test specimens, especially tablets or pills, in accordance with the preambles of claims 1 and 5.

PRIOR ART

In the course of quality control in the fabrication of tablets, the physical properties of tablets, such as, for example, weight, dimensions, disintegration time in a medium and hardness, are determined. For this purpose, tablet testing systems have been developed, each of which can examine numerous tablets from a production cycle in terms of these properties. Tablets of a batch are separated in a storage bin and conveyed on a conveyor belt, for example, from one measurement station to the next.

The hardness of the test specimen is usually measured in a dynamometer cell, whose key components are a pressure piston and a thrust bearing. In order to carry out the hardness test, the test specimen, that is to say, the tablet, is conveyed into the region between the pressure piston and the thrust bearing, whereby the tablet preferably comes into contact with the thrust bearing. The pressure piston is then moved against the thrust bearing and thus against the tablet lying in front of it by means of a stepping motor. The force exerted by the pressure piston with each step of the motor is measured and recorded. This force is constant and very small as long as the pressure piston does not come into contact with the tablet or when it is just pushing it over the testing table without the counterpressure of the thrust bearing. Once the pressure piston comes into contact with the tablet and presses it against the thrust bearing, the force exerted by the pressure piston increases with each step of the stepping motor until the tablet breaks apart. The force employed to break apart the tablet is recorded and serves as a measure of the hardness of the tablet. The abrupt drop in the force employed by the pressure piston in breaking apart the test specimen serves as a termination condition for ending the measurement. The pressure piston is retracted to its starting position and the next tablet can be tested.

In order to afford meaningful, reproducible hardness values, the hardness measurement, that is to say, the crushing of the tablet between the pressure piston and the thrust bearing, should always occur along a defined axis. Attention should be paid to this in the case of tablets that are not symmetrical in shape, if only for the fact that a thickness measurement is often carried out at the same time as the hardness measurement. Consequently, the position of the pressure piston when the hardness measurement is terminated serves as a measure of the thickness. Furthermore, it is entirely possible for tablets of this kind to have different hardness values along different axes.

In the case of tablets with an elongated ellipsoid shape, the alignment during conveyance on the testing table is accomplished passively, for example, by means of a slide, which aligns the tablets transversely to the direction of conveyance. However, irregularly shaped tablets are difficult to align passively in this manner. Therefore, when the hardness of such tablets is measured, greater measurement errors have to be anticipated in the conventional testing systems.

In order to avoid such measurement errors, it is known to actively align the tablets so that their preferred direction, along which the hardness is to be measured, coincides with the direction of movement of the pressure piston against the thrust bearing. For this purpose, the position and alignment of the tablet between the pressure piston and the thrust bearing on a testing table is recorded with a camera and evaluated by means of image processing. The image data make it possible to determine by how many degrees the preferred axis of the test specimen deviates from the direction of movement of the pressure piston and the thrust bearing. This deviation can then be corrected by suitable measures.

A device is known for this purpose with which the tablet is situated on a rotary testing table. The dynamometer cell, in particular the pressure piston and the thrust bearing, are fixed in place. The direction of the hardness measurement is thereby fixed. The testing table is then rotated—under the control of the camera signal—until the preferred axis of the test specimen coincides with the direction of movement of the pressure piston against the thrust bearing. Thus, a hardness measurement is accomplished in the direction of the preferred axis of the test specimen.

However, a drawback of devices of this kind is that the time required to align the test specimen in the direction of movement of the pressure piston is often very long. The reason for this lies in the fact that the movement of the test specimen by rotation of the testing table is very difficult to control owing to the low friction between the test specimen and the testing table.

This can have the consequence that the test specimen often follows the rotary movement of the testing table only partially or not at all. Furthermore, the test specimen, once set in motion, continues to rotate further, even when the testing table stands still. Therefore, after each rotation of the testing table, it is necessary to redetermine the position and preferred axis of the test specimen and, if necessary, to rotate the testing table by way of correction. This is repeated as many times as necessary until the preferred axis of the test specimen coincides, within certain tolerances, with the direction of motion of the pressure piston. Only then can the hardness test be carried out. Therefore, the drawback of this active adjustment of the preferred axis of the test specimen lies in the fact that it often calls for several corrective operating steps for the adjustment; that is to say, the drawback lies in a high computational effort.

TECHNICAL OBJECTIVE

The invention is therefore based on the objective of developing a process and a device for carrying out a hardness test for test specimens, in particular tablets or pills, in which the alignment of the test specimen relative to the pressure piston and the thrust bearing is effectuated in a short time and with little computational effort.

DISCLOSURE OF THE INVENTION AND OF ITS ADVANTAGES

The attainment of the objective consists, in accordance with the invention, in a process for carrying out a hardness test on test specimens, wherein the test specimen is conveyed on a testing table between a pressure piston and a thrust bearing, and the hardness of the test specimen is measured by pressing the pressure piston and the thrust bearing against each other, whereby, in an optical or acoustical manner, the spatial position of a preferred axis of the test specimen is determined. Here, the preferred axis is the axis along which the hardness test is to be carried out—for example, the lengthwise axis of the test specimen.

Furthermore, correction data are determined, which are dependent on these positional data as well as on the position of the pressure piston and the thrust bearing, whereby the position of the pressure piston and the thrust bearing can be determined in the same way as is the position of the test specimen or else electronically from the position of control elements used for moving these elements or from the preceding measurement. On the basis of these correction data, the pressure piston and the thrust bearing are moved relative to the test specimen, whose position is unchanged on the testing table, in such a way that the test direction, that is to say, the direction in which the pressure piston and the thrust bearing press against each other, coincides with the direction of the preferred axis and the thrust bearing is brought into the immediate proximity of the test specimen. The hardness of the test specimen is then determined in the known way by pressing the pressure piston against the test specimen, while the position of the thrust bearing remains unchanged.

Furthermore, the attainment of the objective consists, in a device for carrying out a hardness test on test specimens, this device having a testing table for holding the test specimen as well as a pressure piston and a thrust bearing, which are arranged above the testing table and can move toward each other, wherein the test specimen is situated between the pressure piston and the thrust bearing when this device is in use, and the force employed in pressing the pressure piston and the thrust bearing against each other or a quantity proportional to it can be measured by means of a dynamometer device and the hardness of the test specimen can be determined from this. By means of at least one control element, the pressure piston and the thrust bearing can move in the plane of the testing table in two spatial directions; preferably, they can also move perpendicularly to the plane of the testing table. A device is provided to detect the position of the test specimen lying on the testing table, and in an optical or acoustical manner, this device is capable of recording an image of the measurement site and of using the spatial position of the pressure piston and the thrust bearing as well as a preferred axis of the test specimen to determine correction data, which are emitted as an output signal. The position-detecting device consists, for example, of an optical or acoustical sensor unit—for example, a camera or a sensor array, also one made up of contact sensors—that is coupled to a data processing system. The signals of the unit that scans the measurement site are recorded optically or acoustically, transformed into an image, and evaluated—by means of image processing, for example—to determine the positional information and, ultimately, the correction data. The output signal of the position-detecting device serves to actuate the control element or the control elements in such a way that the test direction is brought to coincide with the direction of the spatially fixed preferred axis of the test specimen.

Preferably, these correction data for controlling the adjustment process are determined several times during the adjustment of the position of the pressure piston and the thrust bearing to the position of the test specimen.

Further advantageous embodiments of the invention are characterized in the other subclaims.

The device of the invention or the process for carrying out a hardness test on test specimens has, in particular, the advantage that the position of the test specimen remains unchanged in space before and after the hardness test. In this way, active movements of the test specimen, for example, through rotation of the testing table, are avoided in an advantageous manner. These movements are difficult to control, since the test specimen is not coupled with the testing table or with another element of the device. The position and the alignment of the test specimen need be determined only once by means of the position-detecting device. On the basis of these data, the pressure piston and the thrust bearing are moved by means of the control elements—preferably under computer control—in such a way that, when they are pressed against each other, their alignment and their direction of movement coincide with the preferred axis of the test specimen. The movement of the pressure piston and the thrust bearing is easy to control in this case and is not dictated by chance, since the pressure piston and the thrust bearing are connected directly or indirectly with the control elements, for example, with motors.

Therefore, in a single operating step, the direction of movement of the pressure piston, relative to the thrust bearing, can be made to coincide with the direction of the preferred axis of the test specimen. In a second operating step, the thrust bearing is preferably advanced toward the test specimen, so that the front surface of the thrust bearing touches the test specimen but does not cause it to move. This starting situation is necessary for carrying out the hardness test since, without the counterpressure of the thrust bearing, the pressure piston would cause the tablet to turn. The pressure piston is then advanced toward the test specimen and the hardness of the tablet is measured in the known manner.

The movement of tablet relative to the pressure piston or the thrust bearing can always be controlled precisely in the device according to the invention.

Therefore, in principle, only a single evaluation of the output signals of the position-detecting device is necessary to determine the position and alignment of the test specimen. The image data, however, are preferably evaluated several times—in particular, before and after rotation of the pressure piston and the thrust bearing—in order to check whether the alignment of the axes has been carried out successfully.

In order to adjust the axes, for example, the angle between the preferred axis of the test specimen and the test direction is determined, and the pressure piston and the thrust bearing are rotated jointly by this angle. Subsequently, the distance of the thrust bearing from the test specimen is determined and the thrust bearing is moved by this distance in such a way that it is situated in the immediate proximity of the test specimen. After this, the hardness test is conducted.

Furthermore, the evaluation of the image data can also be done continually—for example, after each step of the rotating control element. Then, under certain circumstances, it is possible to dispense with a prior determination of the angle of rotation and instead, the coincidence of the axis of the test specimen and the axis connecting the pressure piston and the thrust bearing can be used as the condition for terminating further rotation.

Since the movement of the pressure piston and the thrust bearing can be well controlled, a rapid alignment of the respective axes is accomplished in each case and a subsequent correction of the position of the axes is avoided.

In the device of the invention, the pressure piston and the thrust bearing are situated preferably at most a few millimeters above the table surface of the testing table. Therefore, they can slide or be moved over this table surface with little or absolutely no friction. The distance between the table surface of the testing table and the bottom side of the pressure piston and the thrust bearing is always constant and the bottom side of the pressure piston and the thrust bearing runs parallel to the table surface.

Preferably, the pressure piston and the thrust bearing are joined to each other by means of a holding bracket. Here, they are fastened to the holding bracket by one or more control elements—for example, stepping motors—in such a way that the distance of their respective front surfaces is unchanged. It is possible that both the pressure piston and the thrust bearing can be moved relative to the holding bracket by means of control elements or else that only the pressure piston can be moved. These control elements can serve to advance the thrust bearing directly to the test specimen and to carry out the hardness test through the movement of the pressure piston. To this end, the entire holding bracket can also be adjustable.

Preferably, the holding bracket can be rotated by at least an angle of nearly 180° around an axis of rotation that runs perpendicular to the testing table. Through the rotation of the holding bracket, the axis connecting the pressure piston and the thrust bearing, along which the pressure piston is pressed against the thrust bearing in order to carry out the hardness test, is brought to coincide with the preferred axis of the test specimen.

Preferably, the entire holding bracket can be moved in two spatial directions parallel to the testing table. Accordingly, in order to carry out the hardness test, the axis connecting the pressure piston and the thrust bearing is first brought to coincide with the preferred axis of the test specimen by means of rotation of the holding bracket. The entire holding bracket is then shifted in such a way that the front surface of the thrust bearing lies close to but does not quite touch the test specimen, that is situated at a distance of 0.1 mm to 1 mm from it. If the holding bracket can be moved parallel to the testing table, then it is possible to dispense with a control element for moving the thrust bearing relative to the holding bracket, so that only the control element for advancing the pressure piston to the test specimen is required.

In a further advantageous embodiment of the invention, the holding bracket can be moved perpendicularly to the testing table. This makes it possible to raise the holding bracket together with the pressure piston and the thrust bearing mounted on it in order, for example, to clean the testing table more easily.

In order to allow movement of the holding bracket, the holding bracket is preferably held with a holding arm. The holding arm can hold the holding bracket in a crane-like manner above the testing table, for example. Furthermore, in order to increase the stability of the arrangement, a holding arm that spans the measurement site in a bridge-like manner is advantageous.

A further advantageous embodiment of a dynamometer cell or a pressure piston with a thrust bearing that can be moved freely above the testing table consists, for example, in the attachment of the pressure piston and the thrust bearing to a ring that runs around the measurement site, parallel to the plane of the table. The pressure piston and the thrust bearing are then moved, by means of stepping motors, in a radial direction toward the test specimen, whereby, once again, the thrust bearing is first advanced to the test specimen and, subsequently, the hardness test is carried out by pressing the pressure piston against it. In order to adjust the test direction, either the entire ring is rotated around an axis running perpendicular to the table surface—preferably passing through the center of the ring—or else the pressure piston and the thrust bearing are shifted within the ring, whereby, however, they always lie opposite each other.

The position-detecting device preferably operates optically or else electronically and is, for example, a camera, in particular a CCD camera, or a device for scanning an object by means of laser beams or by means of contact sensors. Furthermore, an acoustical principle of measurement for detecting position is also possible, for example, by means of ultrasound.

In a further embodiment of the invention, the position-detecting device is a matrix made up of optical or contact sensors, which is incorporated into the testing table at least in the region of the measurement site and which is capable of detecting contours of test specimens lying on the testing table. A design of this kind is particularly space-saving and insensitive to vibration. This matrix is, for example, a CCD matrix or a diode array. In order to protect the matrix, the matrix can be covered by a disk made of transparent material—for example glass or acrylic glass.

In a further embodiment of the device, the testing table is at least partially optically transparent, whereby the camera is arranged beneath the testing table. In this case, the testing table consists of acrylic glass, for example, either in its entirety or at least in the region of the measurement site. A design of this kind is space-saving, since it is possible to dispense with holders for the camera above the measurement site.

In order to simplify the evaluation of the camera signal by means of image processing, it is advantageous for the testing table to have a marking, in particular a grid.

Figure 2:
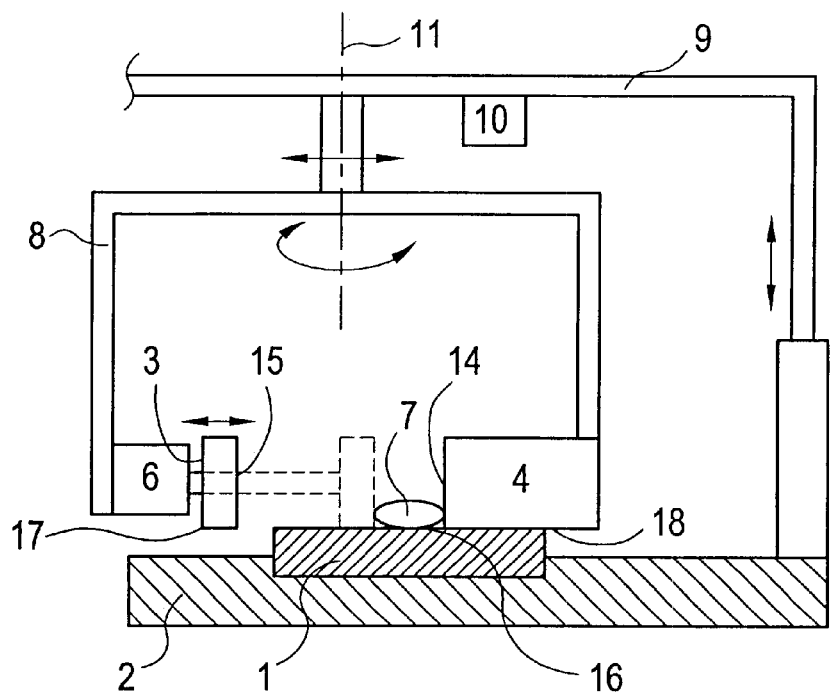
Figure 3:
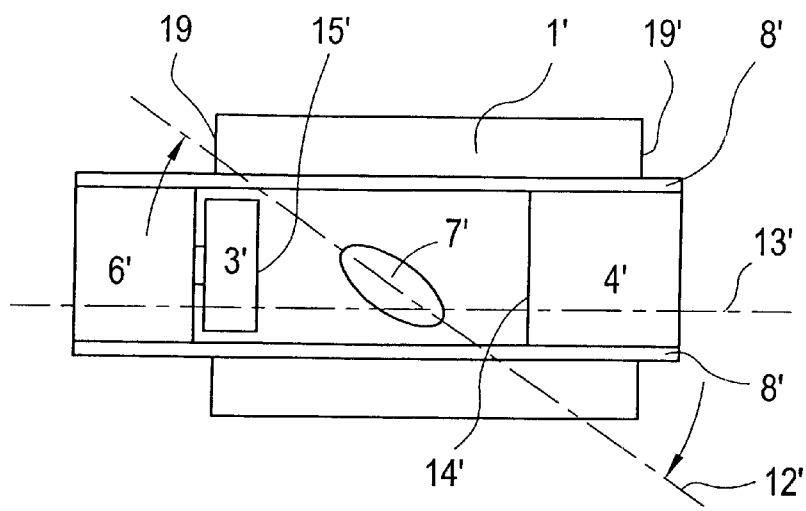
Figure 4:
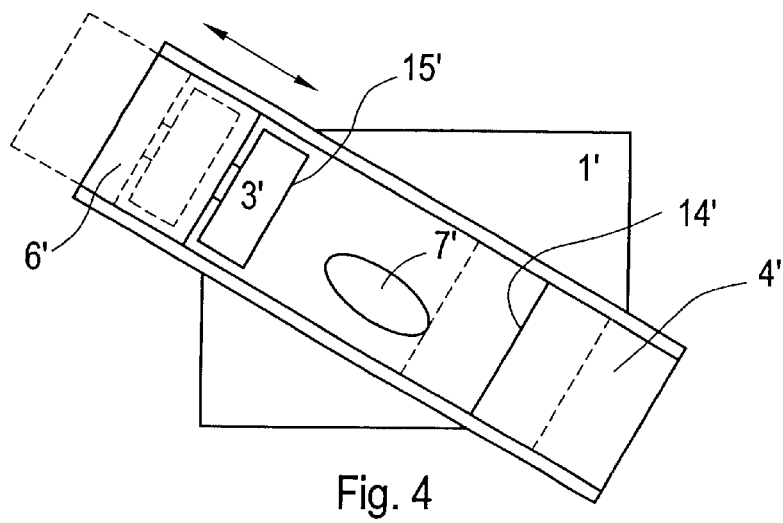
Figure 5:
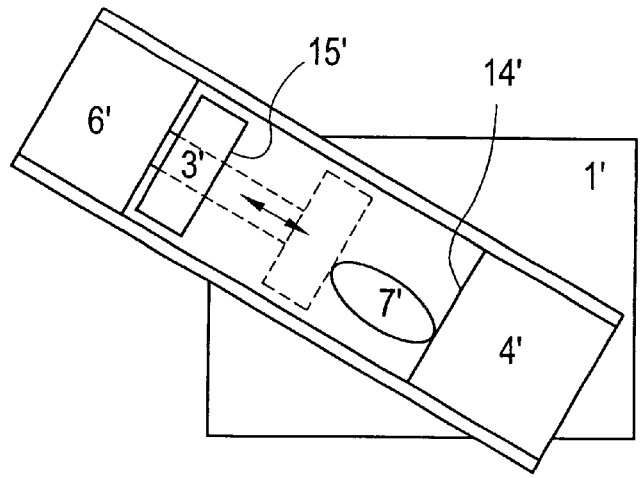
Figure 6:
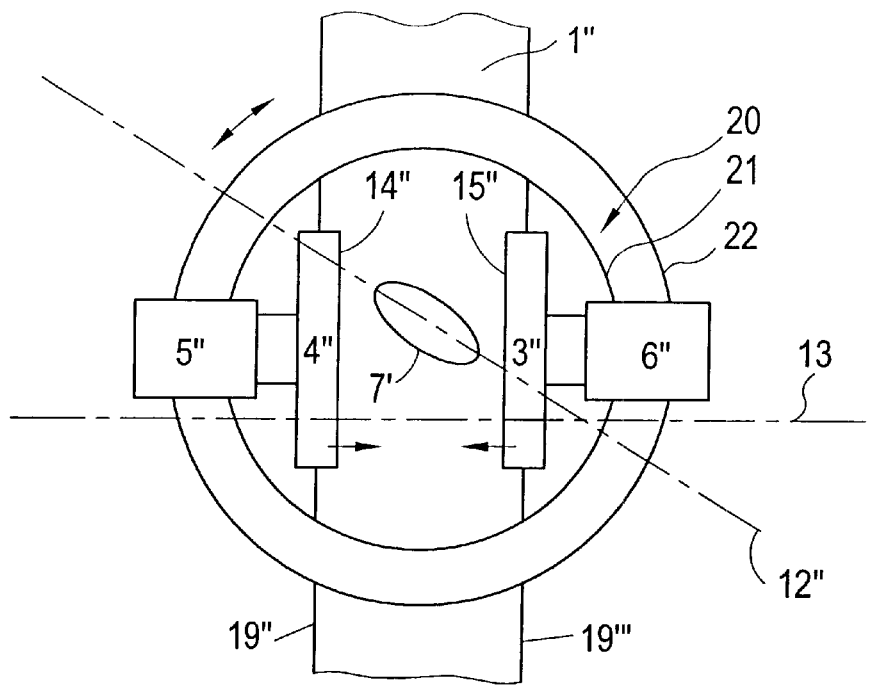
Figure 7:
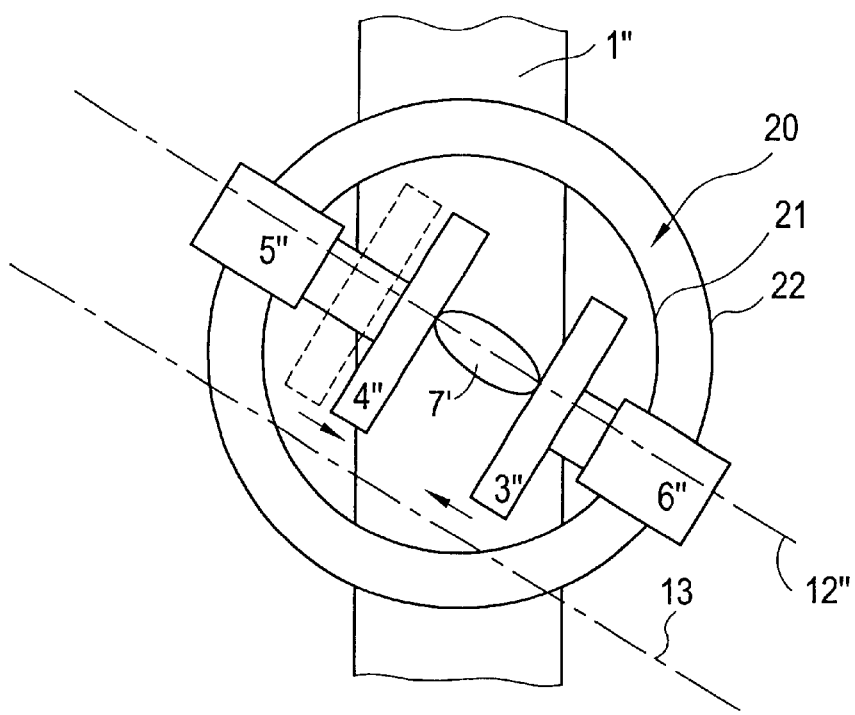
Figure 8:
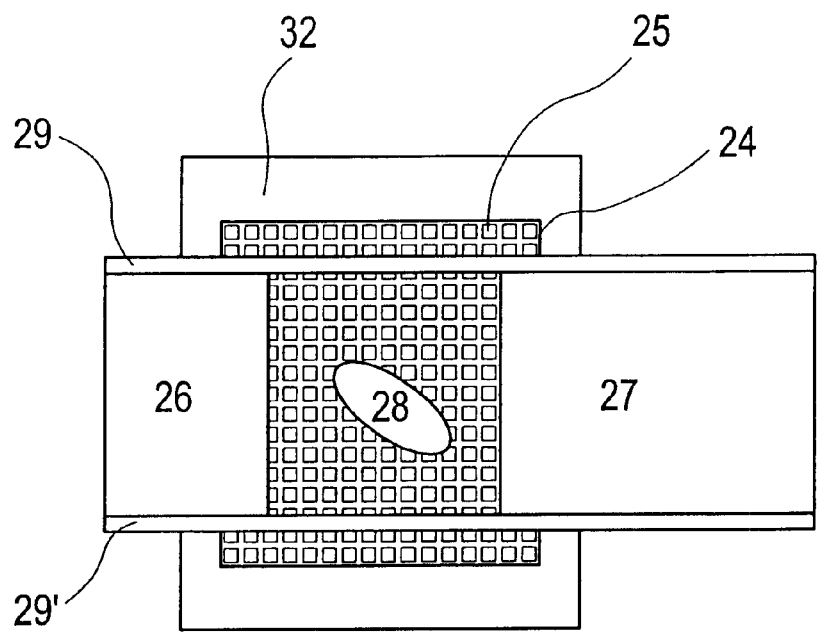
Figure 9:
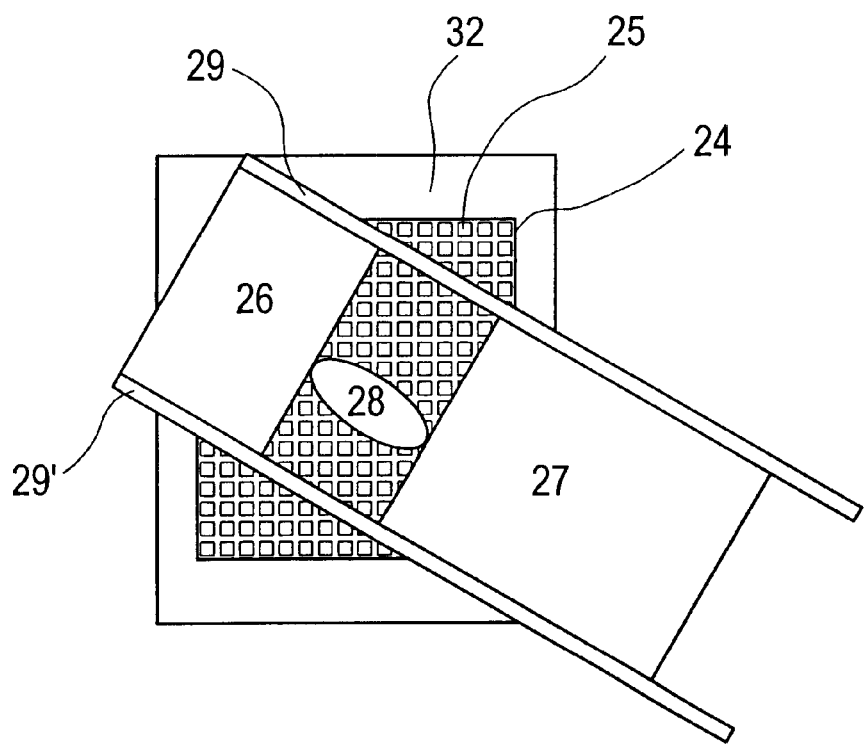
Figure 10:
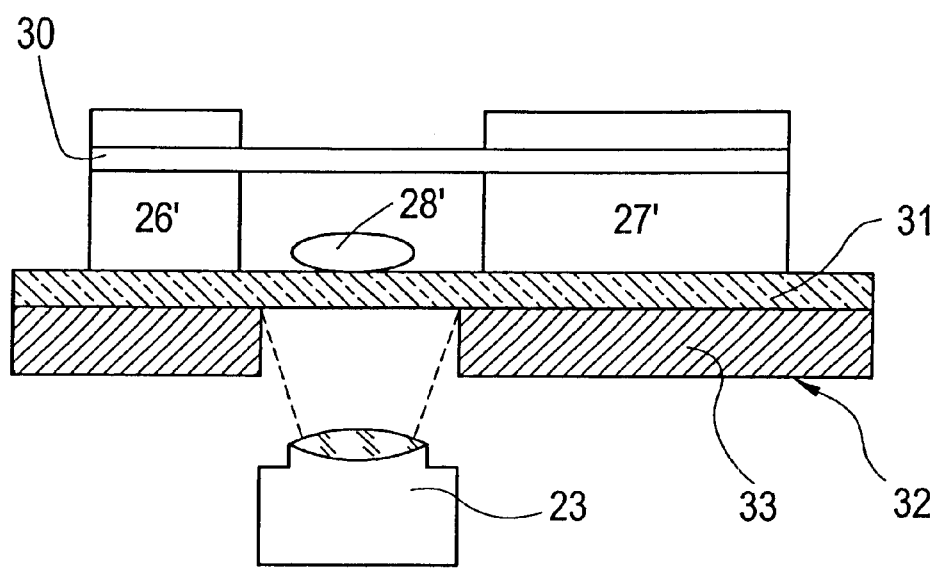

Summary of the drawings, in which the following is shown:

FIGS. 1, 2 a side view of a hardness testing device in two positions of the holding bracket FIGS. 3–5 a view of the testing table of a hardness testing device for illustrating the individual operating steps in carrying out the hardness test FIGS. 6, 7 a top view of a hardness testing device with a ring as the holder FIGS. 8, 9 a top view of the testing table of a hardness testing device with a sensor matrix for detecting positions FIG. 10 a side view of a hardness testing device with a partially transparent testing table and a camera arrangement beneath the latter

PREFERRED EMBODIMENTS

FIGS. 1 and 2 show the side view of a device in accordance with the invention for carrying out a hardness test in two different positions of the holding bracket 8. A test specimen 7, with an ellipsoid shape—for example, a tablet—is situated on a testing table 1. The testing table 1 is embedded in a support table 2. In order to convey the test specimen, either the testing table 1 can be moved relative to support table 2 or the test specimen is conveyed with suitable slides, which are not illustrated here.

A pressure piston 3 and a thrust bearing 4 are situated above the testing table 1, to the side, whereby the pressure piston is joined to a holding bracket 8 by means of a control element 6. The control element 6 is, for example, a stepping motor. By means of the control element 6, the pressure piston 3 can be slid toward the thrust bearing 4 and moved in such a way that it is possible to change the distance between the front surfaces 14 and 15 of the pressure piston 3 and the thrust bearing 4, respectively, whereby, however, the front surfaces are always parallel to each other. In accordance with the current guidelines for testing apparatuses of this kind—for example, in accordance with U.S. patent—the thrust bearing 4 is firmly attached to the holding bracket 8. In this way, inaccuracies in the determination of the hardness of the test specimen are reduced in comparison to the case in which both the pressure piston 3 and the thrust bearing 4 can be moved independently of each other, since a thrust bearing that is rigidly joined to the holding bracket cannot yield to the pressure of the pressure piston, thereby falsifying the measurement.

The holding bracket 8 is fastened to a holding arm 9. The holding arm 9 is arranged on support table 2 in such a way that it can be moved perpendicularly to the table surface 16. In this way, the holding bracket 8, together with the elements arranged on it, can be moved perpendicularly to the table surface. The holding bracket 8 is joined to the holding arm in such a way that it can be rotated around an axis of rotation 11 running perpendicular to the table surface 16. The rotation occurs by means of a motor under computer control. The angle of rotation in this case is at least nearly 180° or more. Through the rotation of the holding bracket 8, the pressure piston 3 and the thrust bearing 4 are aligned in such a way that their direction of movement when they are pressed against each other—namely, the test direction—coincides with the direction of the preferred axis of the test specimen 7. This is illustrated in more detail in FIGS. 2 through 4.

Furthermore, the holding bracket 8 is joined to the holding arm 9 in such a way that it can be moved, together with the pressure piston 3 and the thrust bearing 4, which are attached to it, parallel to the table surface. This movement likewise occurs by means of a motor under computer control. Preferably, when the hardness test is carried out, the test direction is first made to coincide with the preferred direction of the test specimen and then the holding bracket is shifted in such a way that the front surface 14 of the thrust bearing 4 touches the test specimen. FIG. 1 shows the starting position of the device of the invention. FIG. 2 shows the position of the pressure piston 3 and the thrust bearing 4 after the holding bracket has been shifted parallel to the testing table. Broken lines in FIG. 2 show the position of the pressure piston during the hardness measurement itself, that is to say, during the actual crushing of the test specimen 7 between the pressure piston 3 and the thrust bearing 4.

The movement of the pressure piston 3 and the thrust bearing 4 occurs parallel to the table surface 16 of the testing table. The distance between table surface 16 and the bottom sides 17 and 18 of the pressure piston 3 and the thrust bearing 4, respectively, is constant here and is a few millimeters at most. The pressure piston 3 and the thrust bearing 4 can also lie on the testing table. Strong friction between the table surface and the elements lying on it or arranged above it is to be avoided in this arrangement.

Above the testing table 1, there is a camera 10, which records an image of the testing table together with the test specimen 7 lying on it and, if desired, of the pressure piston and the thrust bearing. The camera is, for example, a CCD camera. The image data from the camera 10 are fed to a computer system that is not represented here and that determines the preferred axis of the test specimen by means of image processing. By comparison with the position of the pressure piston and the thrust bearing, which is either a preset starting value, corresponding to the resting position of these elements or else is determined from the camera signals, the angle of rotation by which the holding bracket 8 must be rotated around the axis of rotation 11 is calculated.

After the rotation had been carried out, a camera image can be evaluated once again in order to check the alignment of the pressure piston and the thrust bearing.

The rotation of the holding bracket 8 around the axis of rotation 11 occurs by means of a motor, which is arranged, for example, on the holding arm 9. The control of the motor occurs, for example, through the same computer that also evaluates the image data from the camera 10.

In addition to the position and the alignment of the test specimen 7, the height and/or width of the test specimen can also be measured with camera 10. In this way, it is possible to dispense with corresponding measurement stations for checking the physical properties.

FIGS. 3 and 5 show the top view of the testing table 1' of a device in accordance with the invention in order to illustrate the individual operating steps during performance of a hardness test.

The starting situation is shown in FIG. 3. A test specimen 7' is situated in arbitrary alignment on the testing table 1' between the pressure piston 3' and the thrust bearing 4', which are joined to a holding bracket 8' consisting of two rails. The thrust bearing 4' and the control element 6' for moving the pressure piston 3' are attached rigidly to these rails. The pressure piston 3' can be moved by means of the control element 6' in the direction of the rails in such a way that the distance between the front surfaces 15' and 14' of the pressure piston 3' and the thrust bearing 4', respectively, can be changed. The direction in which the pressure piston 3' and the thrust bearing 4' are pressed against each other is the momentary test direction 13'. The direction along which the hardness test is actually to be carried out is given by the preferred axis 12' of the test specimen 7', which is offset with respect to the momentary test direction 13'. In the relative position of the pressure piston, the thrust bearing, and the test specimen shown, the hardness of the tablet is measured without corrective measures, such as the rotation of the holding bracket 8'; that is to say, the hardness of the tablet is not measured along its preferred direction but rather along the direction 13'. The angle between directions 12' and 13' is arbitrary and here, it is about 30°. The purpose of the device is to make directions 12' and 13' coincide by adjusting the test direction 13' to the preferred direction 12' through rotation of the pressure piston and the thrust bearing.

In FIG. 3, the pressure piston and the thrust bearing are situated in their starting and resting position in such a way that their front surfaces 14' and 15' run parallel to the lateral boundaries 19, 19' of the testing table. However, any arbitrary starting position is possible in principle. The pressure piston 3' and the thrust bearing 4' are affixed on the holding bracket 8'. By means of the control element 6', the pressure piston can be moved in the test direction 13'.

In a first operating step, the preferred axis 12' of the test specimen is determined and is compared with the momentary test direction 13' of the movement of pressure piston and the thrust bearing toward each other. The pressure piston and the thrust bearing are rotated by rotation of the holding bracket 8' around an axis of rotation running perpendicular to the plane of the table in such a way that directions 12' and 13' coincide.

The status of the device after this rotation is illustrated in FIG. 4. Here, the holding bracket 8', together with the pressure piston 3' and the thrust bearing 4', is aligned in such a way that the momentary test direction 13' now coincides with the preferred axis 12' of the test specimen 7'. Here, the test specimen 7' remains lying unchanged in its original position on table 1'. In a second operating stop, the holding bracket 8' is then shifted in the test direction 13' in such a way that the front surface 14' of the thrust bearing 4' is advanced all the way to the test specimen 7'. Since the entire holding bracket 8' is shifted parallel to the table surface, the distance between the pressure piston and the thrust bearing remains constant. This advanced position is shown with broken lines. In the advanced position, the front surface 14' of the thrust bearing 4' touches the test object 7' but does not cause it to move.

In the ensuing operating step, the position of the holding bracket is left stationary and the pressure piston 3' is pushed in the test direction 13', which, in the meantime, coincides with the preferred axis 12' of the test specimen 7', against the thrust bearing 4'. This is illustrated schematically in FIG. 4.

FIG. 4 shows the test specimen 7', whose position has remained unchanged, on the testing table 1. The thrust bearing 4' has been advanced by movement of the holding bracket 8' toward the test specimen 7'. The pressure piston 3', together with the control element 6' associated with it, is now advanced to the test specimen 7'. This position, in which the hardness can now be measured, is represented in broken lines, in contrast to the original position of the pressure piston 3'.

During the hardness measurement, the pressure piston 3' presses the test specimen 7' in the test direction 13' against the thrust bearing 4'. The pressure on the test specimen 7' is increased stepwise until the test specimen 7' breaks apart. The maximum pressure measured just before the test specimen breaks or the corresponding force exerted by the control element 6' or the pressure piston 3' is stored and serves as a measure of the hardness of the test specimen. For structural reasons, the associated dynamometer cell is situated within the thrust bearing, since the motor control for moving the pressure piston is attached to the other side of the holding bracket and is already very heavy as a rule.

After the thrust bearing 4' has been advanced to the test object 7', the hardness of the tablet or of the test specimen is thus measured in the known way.

After the test specimen has broken apart, the pressure piston and the thrust bearing are retracted, preferably to their starting position, as illustrated in FIG. 3. The fragments of the tablet can then be removed and a new test specimen can also be conveyed to the testing table.

FIGS. 6 and 7 are a schematic top view of a further example of a device in accordance with the invention. The hardness tester illustrated here has the elements known from the preceding figures, the testing table 1", the pressure piston 3", and the thrust bearing 4", as well as the control elements 6" belonging to the pressure piston. In contrast to the device illustrated in the preceding figures, the pressure piston 3" and the thrust bearing 4" illustrated here can be moved independently of each other in the test direction 13, whereby the thrust bearing, like the pressure piston, is moved by means of a control element 5".

FIG. 6 shows the starting position of the arrangement for the hardness measurement. A test specimen 7" is situated on the testing table 1" in the region between the pressure piston 3" and the thrust bearing 4". It was conveyed either from above or else from the side into the measurement site by means of, for example, a slide not illustrated here. In order to feed test specimens from the side, the testing table 1" can be designed as an elongated belt or else as a wheel, which leads from a preceding measurement site—for example, weight measurement—to the hardness measurement site.

In the starting and resting position of the pressure piston 3" and the thrust bearing 4", the respective front surfaces 14", 15" are parallel to the sides 19, 19" of the testing table 1". Preferably, the pressure piston 3" and the thrust bearing 4", as illustrated here, are arranged in such a way that the distance of their front surfaces 14", 15" is less than the width of the testing table. In this way, the front surfaces 14", 15" form a lateral boundary of the testing table and prevent the testing sample from inadvertently falling out of the measurement site.

The movement of the pressure piston 3" and the thrust bearing 4" occurs similarly to the way illustrated in FIGS. 3 to 3 [sic]; that is to say, first the test direction 13 is adjusted to the preferred axis 12" and the thrust bearing 4" is advanced—in this case, independently of a holding bracket and thus of the pressure piston—to the test specimen 7" and then the hardness test is carried out by pressing the pressure piston in the test direction against the test specimen. These individual operating steps are shown schematically in FIGS. 6 and 7.

In the embodiment of the invention shown here, the rotational movement of the pressure piston 3" and the thrust bearing 4" takes place around an axis. perpendicular to the plane of the testing table by means of a ring construction 20 consisting of an inner ring and an outer ring, 21 and 22, respectively. The pressure piston and the thrust bearing are held by means of the ring construction, their control elements 5", 6" being firmly joined with the outer ring 22. In order to align the test direction, the entire outer ring 22 is always rotated; for this purpose, it can be designed, for example, as a toothed wheel, which can be rotated by a defined angle, driven by a motor in a precisely controlled manner. Since the pressure piston 3" and the thrust bearing 4" are firmly affixed in the outer ring 22, it is ensured that they always lie diametrically opposite each other and that their front surfaces 14", 15" are always parallel to each other.

The inner ring 21 has a rail or a slit in order to guide the pressure piston 3" and the thrust bearing 4" or the corresponding control elements 5", 6" in a gliding manner. In contrast to the outer ring 22, it remains stationary and serves to support the pressing device (the pressure piston 3" and the thrust bearing 4", together with control elements 5", 6"). It can be designed as a cylinder.

The ring construction 20 is designed in such a way that, in the region of the testing table 1", the feeding and removal of test specimens or of the fragments, respectively, is possible without difficulty; for example, the inner ring 21 has openings in the region of the table and there is a large distance between the outer ring 22 and the testing table.

If the pressure piston 3" and the thrust bearing 4" are of roughly the same width as the measurement site or the same width as the testing table, a translatory movement of the unit consisting of the pressure piston 3' and the thrust bearing 4' can be dispensed with through the movement of the ring parallel to the testing table 1". All of the testing samples in the region of the measurement site can then be crushed by a pure rotational movement of the pressure piston 3" and the thrust bearing 4", followed by advancing of the thrust bearing to the test specimen in the direction of its preferred axis. To this end, however, one should avoid tipping of the pressure piston 3" and the thrust bearing 4" toward their respective control elements 6' and 5' as a result of the lever effect during the crushing of a test specimen that does not meet the front surfaces at their centers.

FIGS. 8 and 9 show a top view of the testing table 32 of a hardness testing device that has a sensor matrix 24 as a device for detecting the position of the test specimen. The matrix 24 consists of a large number of regularly arranged optical sensor elements 25, which are incorporated into the testing table 32. In order to protect the sensor elements 25, the matrix is covered with an optically transparent material, whereby the top side of the testing table is smooth and entails as little friction as possible.

Through appropriate evaluation of the measurement signals of matrix 25, the position of a test specimen 28 on the testing table is determined. The measuring signals are generated, for example, by optical sensors when a shadow is projected onto the active surface of the sensor elements. By association of the signals with the spatial position of the sensors, the position and contour of the test specimen can be reconstructed. In this way it is also possible to determine its preferred direction along which the hardness is to be tested.

Furthermore, the matrix 25 makes it possible to determine the position of the pressure piston 26 and the thrust bearing 27, since these are likewise situated above the region covered by the matrix. In this way, correction data can be determined for adjusting the position of the pressure piston 26 and the thrust bearing 27 to the position of the tablet by comparing their respective spatial positions. Likewise, the adjustment of the positions can be carried out in an iterative process by repeated evaluation of the output signals of the sensor matrix.

FIG. 8 shows the starting position at the beginning of the hardness test. The test specimen 28 is situated on the testing table in the region between the pressure piston 26 and the thrust bearing 27, which are joined to each other by two rails, 29 and 29', which function as holding brackets. In FIG. 9, the adjustment of the positions of the pressure piston 26 and the thrust bearing 27 to the position of tablet 28, which is unchanged from FIG. 8, has already been carried out. The front surface of the thrust bearing 27 is situated in immediate proximity to the test specimen 28, but does not touch it initially, since, in that way, its position could be changed and would have to be adjusted anew. In FIG. 9, the pressure piston 26 is likewise advanced to the immediate proximity of the tablet. In the device shown here, the control elements for moving the pressure piston are situated in the region of the thrust bearing 27, whereby the force is imparted through rails 29, 29', which are joined firmly to the pressure piston 26 and which pull it toward the thrust bearing 27 during the hardness test. The test direction is preset through the alignment of rails 29, 29'.

FIG. 10 shows a side view of a hardness testing device with a partially transparent testing table 32', consisting of a transparent plate 31 and a support table 33, wherein, beneath the latter, there is a camera 23. On the testing table 32', there is a test specimen 28' in the measurement site between the pressure piston 26' and the thrust bearing 27'. In the region beneath the measurement site, there is a recess in the support table 33, so that the test specimen is visible to the camera 23 through the transparent plate 33. In this way, through an evaluation of the camera signal, information can be obtained on the momentary positions of the test specimen 28', the pressure piston 26', and the thrust bearing 27'.

The transparent plate 31 consists of a smooth material that is as resistant as possible to scratching and offers as little friction as possible, preferably glass or acrylic glass. The camera 23 is a common video camera or a CCD camera. The pressure piston 26' and the thrust bearing 27' are joined to each other by a holding bracket 30 made, for example, of two rails. By means of the holding bracket 30 and control elements arranged in the region of the thrust bearing—e.g. stepping motors—the pressure piston is pulled toward the thrust bearing. The recording and, if necessary, evaluation of the signals of the dynamometer cell likewise take place in the region of the thrust bearing.

Commercial Application

The invention is commercially applicable, in particular, in the course of quality control in the fabrication of shaped pharmaceutical solids of all kinds.

List of Reference Numerals 1, 1', 1", 32, 32' testing table
2, 33 support table
3, 3', 3", 26, 26' pressure piston
4, 4', 4", 27, 27' thrust bearing
5", 6, 6', 6" control element
7, 7', 7", 28, 28' test specimen (tablet)
8, 8', 30 holding bracket
9 holding arm
10 position-detecting device
11 axis of rotation
12, 12', 12" preferred axis
13, 13' test direction
14, 14', 14",
15, 15', 15" front surface (pressure piston or thrust bearing)
16 table surface (testing table)
17, 18 bottom (pressure piston or thrust bearing)
19, 19' sides (testing table)
20 ring construction
21 inner ring
22 outer ring
23 camera
24 matrix
25 sensor element
29, 29' rail
31 transparent plate

What is claimed is:

1. Process for conducting a hardness test on test specimens (7, 7', 7", 28, 28'), especially tablets or pills, wherein the test specimen is conveyed on a testing table (1, 1', 1", 32, 32') between a pressure piston (3, 3', 3", 26, 26') and a thrust bearing (4, 4', 4", 27, 27") and the hardness of the test specimen is measured by pressing the pressure piston (3, 3', 3", 26, 26') and the thrust bearing (4, 4', 4", 27, 27') against each other, characterized in that, a) the spatial position of a preferred axis (12, 12', 12") of the test specimen (7, 7', 7", 28, 28') is determined with the aid of optical, electronic or acoustical means;

b) correction data are determined, which are dependent on positional data as well as on the position of the pressure piston and the thrust bearing;

c) on the basis of these correction data, the pressure piston (3, 3', 3", 26, 26') and the thrust bearing (4, 4' 4", 27, 27') are moved relative to a test specimen, whose position is unchanged on the testing table, in such a way that the test direction (13), namely the direction in which the pressure piston (3, 3', 3", 26, 26') and the thrust bearing (4, 4', 4", 27, 27') press against each other, coincides with the direction of the preferred axis (12, 12', 12") and the thrust bearing is brought into the immediate proximity of the test specimen;

d) the hardness of the test specimen is then determined in a conventional way by pressing the pressure piston against the test specimen, while the position of the thrust bearing remains unchanged.

2. Process according to claim 1, characterized in that the position is detected in an optical, electronic or acoustical manner, whereby the measured signals are converted into an image of a measurement site, on the basis of which the correction data are determined by means of image processing.

3. Process according to claim 1, characterized in that several times during an adjustment of a position of the pressure piston (3, 3', 3", 26, 26') and the thrust bearing (4, 4', 4", 27, 27) to the position of the test specimen, correction data are determined for purposes of controlling the adjustment process and the adjustment is carried out iteratively.

4. Process according to claim 1, characterized in that the angle between the preferred axis (12, 12', 12") of the test specimen (7, 7',7", 28, 28') and the test direction (13) is determined, the pressure piston (3, 3', 3", 26, 26') and the thrust bearing (4, 4', 4", 27, 27') are rotated jointly by this angle, subsequently, the distance of the thrust bearing (4, 4', 4", 27, 27') from the test specimen is determined and the thrust bearing (4, 4', 4", 27, 27') is moved by this distance in such a way that it is situated in the proximity of the test specimen and then the hardness test is conducted.

5. Device for conducting a hardness test on test specimens (7, 7', 7", 28, 28') for conducting the process according to claim 1, having a testing table (1, 1', 1", 32, 32') for holding the test specimen (7, 7', 7", 28, 28') as well as a pressure piston (3, 3', 3", 26, 26') and a thrust bearing (4, 4', 4", 27, 27'), which are arranged above the testing table (1, 1', 1", 32, 32') and which move toward each other, wherein the test specimen (7, 7', 7", 28, 28') is situated between the pressure piston (3, 3', 3", 26, 26') and the thrust bearing (4, 4', 4", 27, 27') while this device is in use, and a force employed in pressing the pressure piston (3, 3', 3", 26, 26') and the thrust bearing (4, 4', 4", 27, 27") against each other or a quantity proportional to it is measured by means of a dynamometer device and the hardness of the test specimen is determined from this, characterized by the following features:

a) at least one control element (5", 6, 6', 6") with which the pressure piston (3, 3', 3", 26, 26') and the thrust bearing (4, 4', 4", 27, 27") move in the plane of the testing table in two spatial directions;

b) a position-detecting device (10) of the test specimen (7, 7', 7", 28, 28') lying on the testing table (1, 1', 1", 32, 32'), which, in an optical or acoustical manner, records an image of the measurement site and of using a spatial position of the pressure piston (3, 3', 3", 26, 26') and the thrust bearing (4, 4', 4", 27, 27') as well as a preferred axis (12, 12', 12") of the test specimen (7, 7', 7", 28, 28') to determine correction data, which correction data are emitted as an output signal;

c) the output signal of the position-detecting device (10) serves to actuate the control element (5", 6, 6', 6") or the control elements in such a way that the test direction (13), i.e. the direction of movement of the pressure piston (3, 3', 3", 26, 26') and the thrust bearing (4, 4', 4", 27, 27') against each other, is brought to coincide with the direction of the spatially fixed preferred axis (12, 12', 12") of the test specimen 7, 7', 7", 28, 28').

6. Device according to claim 5, characterized in that the position-detecting device (10) comprises an image processing mechanism, which image processing mechanism is coupled to a data processing system that processes images.

7. Device according to claim 5, characterized in that the pressure piston (3, 3', 3", 26, 26') and the thrust bearing (4, 4', 4", 27, 27') are joined to each other by means of a holding bracket (8, 8', 30) in such a way that the distance of their respective front surfaces (14, 14', 14" or 15, 15', 15") is adjustable and the holding bracket (8) is rotated by at least an angle of nearly 180' around an axis of rotation (11) that runs perpendicular to the testing table (1, 1', 1", 32, 32'), whereby the holding bracket (8, 8', 30) is held above the testing table with a holding arm (9).

8. Device according to claim 5, characterized in that the pressure piston (3, 3', 3", 26, 26') and the thrust bearing (4, 4', 4", 27, 27') are attached across from each other to a ring (20, 21, 22) that runs around the measurement site, parallel to the plane of the table, and the distance between their respective front surfaces (14, 14', 14" or 15, 15', 15") is changed.

9. Device according to claim 8, characterized in that in order to adjust the test direction, an entire ring (20, 21, 22) is rotated or the pressure piston (3, 3', 3", 26, 26') and the thrust bearing (4, 4', 4", 27, 27') is rotated within the ring (20, 21, 22) or guided by the ring (20, 21, 22).

10. Device according to claim 8, characterized in that the ring has lateral recesses to feed test specimens or remove fragments of test specimens.

11. Device according to claim 7, characterized in that the holding bracket (8, 8) or the ring (20, 21, 22) is moved perpendicularly to the testing table.

12. Device according to claim 7, characterized in that the pressure piston (3, 3', 3", 26, 26') or the thrust bearing (4, 4', 4", 27, 27') is moved relative to the holding bracket (8, 8', 30) or relative to the ring (20, 21, 22) by means of stepping motors.

13. Device according to claim 7, characterized in that the thrust bearing (4, 4', 4", 27, 27') is firmly attached to the holding bracket (8, 8', 30), whereby the pressure piston (3, 3', 3", 26, 26') is moved against the thrust bearing by means of a stepping motor.

14. Device according to claim 1, characterized in that the testing table (1, 1', 1", 32, 32') has a marking, in particular a grid, in order to simplify an evaluation of signals of the position-detecting device (10) for purposes of determining the position and the preferred axis (12, 12', 12") of the test specimen (7, 7', 7", 28, 28').

15. Device according to claim 1, characterized in that the position-detecting device (10) is a CCD camera, which is coupled to a data processing system.

16. Device according to claim 15, characterized in that the testing table is at least partially optically transparent, whereby the camera (23) for detecting the position of the test specimen is arranged beneath the testing table.

17. Device according to claim 5, characterized in that the position-detecting device (10) is a device for scanning an object, here the test specimen, by means of laser beams, which is coupled to a data processing system.

18. Device according to claim 5, characterized in that the position-detecting device (10) is a matrix (24) made up of optical or contact sensors (25) and coupled to a data processing system which is incorporated into the testing table at least in a region of the measurement site and which is furnished for detecting contours of test specimens lying on the testing table.

19. Device according to claim 18, characterized in that the matrix is a CCD matrix or a diode array.

20. Device according to claim 1, characterized in that the position of the test specimen is determined acoustically by means of ultrasound.

* * * * *